United States Patent [19]
Panayotatos

[11] Patent Number: 5,716,803
[45] Date of Patent: *Feb. 10, 1998

[54] RECOMBINANT PROTEIN PRODUCTION WITH REDUCED EXPRESSION OF SELECTABLE MARKERS

[75] Inventor: Nikos Panayotatos, Orangebourg, N.Y.

[73] Assignee: Regeneron Pharmaceuticals, Inc., Tarrytown, N.Y.

[*] Notice: The term of this patent shall not extend beyond the expiration date of Pat. No. 5,256,568.

[21] Appl. No.: 6,863

[22] Filed: Jan. 21, 1993

Related U.S. Application Data

[63] Continuation of Ser. No. 478,338, Feb. 12, 1990, Pat. No. 5,256,568.

[51] Int. Cl.$^6$ .................. C12P 21/00; C12N 15/63; C12N 15/65; C07H 21/04
[52] U.S. Cl. .................. 435/69.1; 435/69.1; 435/91.4; 435/91.41; 435/91.42; 435/320.1; 536/24.1
[58] Field of Search .................. 435/69.1, 320.1, 435/91.4; 536/24.1

[56] References Cited

U.S. PATENT DOCUMENTS

| | | | |
|---|---|---|---|
| 4,530,901 | 7/1985 | Weissmann | 435/69.51 |
| 4,716,112 | 12/1987 | Panayotatos | 435/69.1 |

FOREIGN PATENT DOCUMENTS

| | | | |
|---|---|---|---|
| 204401 | 12/1986 | European Pat. Off. | |
| WO 85/04419 | 10/1985 | WIPO | |

OTHER PUBLICATIONS

DeBoer et al., 1982, *Promoters: Structure and Function* pp. 462–481.
Nakamura & Inouye, 1979, *Cell* 18:1109–1117.
Sambrook et al. (ed.), *Molecular Cloning: A Laboratory Manual*, Cold Spring Harbor Laboratory, Cold Spring Harbor, NY, pp. 1.5–1.6, 1989.
Schaller et al., 1975, Proc. Natl. Acad. Sci. U.S.A. 72(2):737–741.
Shine and Dalgarno, 1975, Nature 254:34–38.
Pribnow, 1975, Proc. Natl. Acad. Sci. U.S.A. 72(3):784–788.
Takanami et al., 1976, Nature 260:297–302.
Seeburg et al., 1977, Eur. J. Biochem. 74:107–113.
Uhlin and Nordstrom, 1977, Plasmid 1:1–7.
Rosenberg et al., 1979, Ann. Rev. Genet. 13:319–353.
Steitz, 1980, in *Ribosomes: Structure, Function and Genetics*, Chambliss et al., (eds.), University Park Press, Baltimore, MD, pp. 479–495.
Panayotatos and Truong, 1981, Nucl. Acids. Res. 9(21):5679–5687.
Wong et al., 1982, Proc. Natl. Acad. Sci. U.S.A. 79:3570–3574.
Kalderon et al., 1982, Nucl. Acids Res. 10(17):5161–5171.
Stormo et al., 1982, Nucl. Acids Res. 10(9):2971–2996.
Matteucci and Heyneker, 1983, Nucl. Acids Res. 11(10):3113–3121.
Oostra et al., 1983, Nature 304:456–459.
Panayotatos et al., 1983, J. Cell. Biochem. Suppl. 7B:109 (Abstr. 765).
Panayotatos, 1984, Nucl. Acids Res. 12(6):2641–2648.
Gold et al., 1984, Proc. Natl. Acad. Sci. U.S.A. 81:7061–7065.
Cowing et al., 1985, Proc. Natl. Acad. Sci. U.S.A. 82:2679–2683.
Buell and Panayotatos, 1986, in *Gene to Protein: Steps Dictating the Maximal Level of Gene Expression*, Reznikoff and Gold (eds.), Butterworths, Stoneham, MA, pp. 345–363.
Derbyshire et al., 1986, Gene 46:145–152.
Stewart et al., 1986, Plasmid 15:172–181.
Panayotatos, 1987a, in *Plasmids, A Practical Approach*, Hardy (ed.), IRL Press, Washington, D.C., pp. 163–176.
Panayotatos, 1987b, in *Vectors A Survey of Molecular Cloning Vectors and their Uses*, Rodriguez and Denhardt (eds.), Butterworths, Boston, MA, pp. 227–235.
Panayotatos, 1988, Gene 74:357–363.
Studnicka, 1988, Biochem. J. 252:825–831.
Kues and Shahl, 1989, Microbiol. Rev. 53(4):491–516.
Leibrock et al., 1989, Nature 341:149–152.
Stöckli et al., 1989, Nature 342:920–923.

*Primary Examiner*—Jasemine C. Chambers
*Assistant Examiner*—Scott D. Priebe
*Attorney, Agent, or Firm*—Pennie & Edmonds

[57] ABSTRACT

The present invention relates to expression of recombinant proteins by use of a bacterial host expression vector which expresses a recombinant protein under the control of a first regulatory expression element, and expresses a selectable marker under the control of a second regulatory expression element, which second element is mutated such that expression of the selectable marker is at reduced levels relative to that directed by such an unmutated expression element. Such an expression vector in a suitable bacterial host (a) allows ease of purification of the recombinant protein of interest ("the recombinant protein") since less selectable marker is present to interfere with the purification of the recombinant protein, and (b) increases the amount of recombinant protein that is produced by the bacterial host cell. Furthermore, in an embodiment in which the selectable marker is an antibiotic resistance gene, expression according to the present invention ensures that only the minimal necessary levels of antibiotic will be used for selection during fermentation. The invention provides expression vectors, host-vector expression systems (comprising the expression vector in a bacterial host in which it can be expressed), and methods relating thereto.

19 Claims, 5 Drawing Sheets

```
DNA PRIMER:    5'  C C C T C T G G G A T C C C T T G G G A A G  3'
                                    \_______/
                                     BamHI

LEFT REPEAT:   5'  C C C T C T G G T A A G G T T G G G A A G  3'

MODEL:                              T  t a a
                                          a g
```

RECOMBINANT PROTEIN PRODUCTION WITH REDUCED EXPRESSION OF SELECTABLE MARKERS

This is a continuation of application Ser. No. 07/478,338 filed Feb. 12, 1990 now U.S. Pat. No. 5,256,568, which is incorporated by reference herein in its entirety.

TABLE OF CONTENTS

1. Introduction
2. Background of the Invention
2.1. Recombinant Protein Production
2.2. Expression Vector Variations and Requirements
2.3. Site-Directed and Site-Specific Mutagenesis
2.4. Promoter Structure
3. Summary of the Invention
3.1. Definitions
4. Description of the Figures
5. Detailed Description of the Invention
6. Example: Recombinant Protein Production with Minimal-Antibiotic-Resistance Vectors
  6.1. Materials and Methods
    6.1.1. General Techniques
    6.1.2. Bacterial Strains
    6.1.3. Plasmids
  6.2. Results
    6.2.1. Site-Directed Mutagenesis of the Promoter for the Kanamycin Resistance Gene (KanR)
    6.2.2. Decrease in Kanamycin Resistance
    6.2.3. Recombinant Protein Production
  6.3. Discussion
7. Example: Site-Specific Mutagenesis of the Ampicillin Promoter
8. Deposit of Microorganism

1. INTRODUCTION

The present invention relates to compositions comprising vectors for protein expression in the field of recombinant DNA technology. The invention provides compositions comprising vectors which minimally express selectable markers in combination with the expression of a sequence encoding at least one peptide or protein, in cells containing the vectors. The invention also relates to the uses of such vectors for the expression and production of high levels of at least one specific peptide or protein. In a particular embodiment, the selectable marker is a protein providing antibiotic resistance.

2. BACKGROUND OF THE INVENTION

2.1. RECOMBINANT PROTEIN PRODUCTION

Recombinant DNA technology involves insertion of specific DNA sequences into a DNA vehicle called a vector to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made.

Regardless of the method used for construction, the recombinant DNA molecule must be compatible with the host cell, i.e. capable of autonomous replication in the host cell or stably integrated into one or more of the host cell's chromosomes. The recombinant DNA molecule should preferably also have a marker function which allows the selection of the desired recombinant DNA molecule(s) in host cells. In addition, if all of the proper replication, transcription, and translation signals are correctly arranged on the recombinant vector, the foreign gene will be properly expressed in, e.g. the transformed bacterial cells, or in permissive cell lines or hosts infected with a recombinant virus or carrying a recombinant plasmid having an appropriate origin of replication.

Different genetic signals and processing events control levels of gene expression such as DNA transcription and messenger RNA (mRNA) translation. Transcription of DNA is dependent upon the presence of a promoter, which is a DNA sequence that directs the binding of RNA polymerase and thereby promotes mRNA synthesis. The DNA sequences of eukaryotic promoters differ from those of procaryotic promoters. Furthermore, eukaryotic promoters and accompanying genetic signals may not be recognized in or may not function in procaryotic systems and furthermore, procaryotic promoters are not recognized and do not function in eucaryotic cells.

Similarly, translation of mRNA in procaryotes depends upon the presence of the proper procaryotic signals, which differ from those of eukaryotes. Efficient translation of mRNA in procaryotes requires a ribosome binding site called the Shine-Dalgarno (S/D) sequence on the mRNA [Shine and Dalgarno, Nature 254:34 (1975)]. This sequence is a short nucleotide sequence of mRNA that is located before the start codon, usually ATG, which encodes the amino-terminal methionine of the protein. The S/D sequences are complementary to the 3' end of the 16S ribosomal RNA (rRNA), and probably promote binding of mRNA to ribosomes by duplexing with the rRNA to allow correct positioning of the ribosome on the mRNA.

Although the Shine/Dalgarno sequence, consisting of the few nucleotides of complementarity between the 16S ribosomal RNA and mRNA, has been identified as an important feature of the ribosome binding site [Shine and Dalgarno, id.; Steitz in Ribosomes: Structure, Function and Genetics, ed. Chambliss et al., Baltimore, Md., University Park Press, pp. 479–495 (1980)], computer analysis has indicated that approximately one hundred nucleotides surrounding the ATG initiating codon are involved in ribosome/mRNA interaction as indicated by proper prediction of translation start signals [Stormer et al., Nucl. Acids Res. 10: 2971 (1982); Gold et al., Proc. Natl. Acad. Sci. 81: 7061 (1984)].

Successful expression of a cloned gene thus requires sufficient transcription of DNA, translation of the mRNA and possibly post-translational modification of the protein using the host cell synthetic machinery for both mRNA synthesis and protein synthesis.

2.2. EXPRESSION VECTOR VARIATIONS AND REQUIREMENTS

Expression of a recombinant protein is affected by the efficiency with which the multiple gene copies are transcribed into mRNA as well as the efficiency with which the desired mRNAs are translated into protein. Degradation of mRNA and protein will adversely affect high production of recombinant protein. Expression is also affected by the number of copies of genes coding for the protein of interest that are contained within a single cell. Generally, the more gene copies there are, the more protein that can be produced up to a level wherein the synthetic machinery is fully saturated.

Plasmid cloning vehicles (plasmids) can have a high copy number that can be modulated by different factors, for example, regulation of the concentration of RNAs that are involved in initiation of plasmid DNA synthesis (see, for example, U.S. Pat. No. 4,716,112, issued Dec. 29, 1987). In addition, plasmids provide a well characterized foundation vector for genetic engineering since the DNA of many plasmids has been completely sequenced.

Vectors must have, at a minimum, a replicon. A replicon is a region necessary for stable replication and copy number control of the plasmid. Plasmid copy number can vary from one or two copies per cell to several hundred, depending on the plasmid selected. Indeed, plasmids with mutant runaway replication have been produced that are present in thousands of copies per cell. These mutants however, usually result in cell lethality.

Recombinant vectors used for high level expression suitable for fermentation and commercial protein production have efficient promoters for transcription initiation preceding the expressed protein. High level protein production is correlated with producing sufficient amounts of mRNA using the host cell transcription machinery. Strong bacterial promoters that are frequently used for mRNA production of high amounts of expressed recombinant proteins are the $P_L$ promoter of lambda, the lacUV$_5$ E. coli promoter, the promoter for the E. coli tryptophan operon $P_{TRP}$, or the recombinant trp-lac promoter termed $P_{TAC}$ or $P_{TRC}$. These promoters share the characteristics of being strong promoters that can result in recombinant proteins expressed as 30–50% of the total cellular protein. Each of these promoters can also be regulated.

An optimal vector will also have an appropriate ribosome binding site to allow efficient mRNA translation. Included within the ribosome binding site is the region of homology of the mRNA with the 3' end of 16S ribosomal RNA that is known as the Shine/Dalgarno sequence. Within the mRNA, the ribosome binding site can be affected by intramolecular secondary structure interactions with the protein coding region, which interaction can affect the efficiency of translation both positively and negatively.

An optimal expression vector will have a selectable marker to allow rapid identification of host cells containing the vector. The type of selectable marker that is commonly used for bacterial expression systems is an antibiotic resistance gene, e.g. ampicillin, tetracycline, kanamycin. However, disadvantages result when plasmid encoded proteins like the antibiotic resistance markers are present on the vectors. The use of large amounts of antibiotics in commercial fermentation processes favors development of antibiotic resistance in the environment and potentially in pathogenic organisms upon disposal of the fermentation medium. Such resistance jeopardizes the therapeutic qualities of the very antibiotics used for selection. In addition, the antibiotic resistance markers used in vectors provide a large amount of a specific antibiotic resistance protein that can complicate protein purification of the desired recombinant protein. Moreover, some antibiotics cause severe reactions in individuals which can result in anaphylactic shock and even death, necessitating absolute preclusion of these antibiotics in therapeutic preparations.

2.3. SITE-DIRECTED AND SITE-SPECIFIC MUTAGENESIS

The technique of site-specific mutagenesis was an improvement on in vivo mutagenesis techniques. The ability to chemically synthesize DNA allowed scientists the opportunity to develop mutations at any base in a given nucleic acid sequence.

Recombinant DNA technology provided methods of easily deleting large blocks of sequence by juxtaposing otherwise separated restriction enzyme sites within a sequence to crudely map regions of interest. Chemical mutagenesis is useful but is limited in scope to alteration of the nucleotides that are affected by the chemical, e.g. C to T transitions produced by sodium bisulfite. Oligonucleotide site-specific mutagenesis allows mutations at a specific nucleotide in a DNA sequence by construction of a mutated oligonucleotide that includes modifications at the site of interest. Random mutagenesis techniques allow the rapid and easy generation of a large number of a variety of uncharacterized mutations.

Matteucci and Heyneker [Nucl. Acids Res. 11:3113 (1983)] used what they termed "ambiguous synthesis" to mutagenize a 9 bp sequence preceding the initiation codon for bovine growth hormone. In their method, oligonucleotides were manually synthesized on a cellulose support using monomer addition triester chemistry. During synthesis, the three precursors not specified by the starting sequence were present at 8% while the specified sequence precursor was present at 75% allowing ambiguous incorporation of precursor at a predictable frequency at each cycle of synthesis. The ambiguous oligonucleotides were added to a specially prepared vector, ligated, transformed and screened for nonhomology to the wild type starting sequence. DNAs containing nonhomologous sequences were sequenced to obtain frequency of mutation data.

Derbyshire et al. [Gene 46:145 (1986)] described an automated method of producing and cloning single stranded oligonucleotides that direct a specific change at a chosen site of a fragment of known DNA sequence. A mixed sequence 28 mer preparation was made by contaminating each of the monomer reservoirs with each of the other precursors at 1/54th the concentration of the wild type precursor monomer. The authors used a probability equation that predicts the probability of mutations for any length of oligonucleotide using a wide range of relative concentrations of mutant and wild type precursor monomers. The observed yield of mutations for single mutations (23), double mutations (8), triple mutations (4) and quadruple mutations (1) as compared to wild type sequence (18) correlated remarkably well with the yield predicted by the equation.

Oostra et al., Nature 304:456 (1983), probed the sequence requirements of middle-T antigen amino acids 305–318 for transformation effectiveness of polyoma virus using site-directed and site-specific mutagenesis. Deletion loop site-directed mutagenesis was accomplished using the methods of Kalderon et al., Nucl. Acids Res. 10: 5161 (1982) and treatment of heteroduplex molecules with sodium bisulfite. Site-directed mutation frequency was 1 in 20 molecules. A 19 residue oligonucleotide, corresponding to nucleotides 1,170 to 1,188 of polyoma virus DNA except that T rather than A was present at residue 1,178, was synthesized using the solid phase phosphotriester method of Edge et al., Nature 292: 756 (1981) to produce a site-specific mutation. A gapped heteroduplex molecule was formed from appropriate plasmid DNAs and hybridized to the synthetic oligonucleotide. The desired site-specific mutant was detected by restriction enzyme mapping where the loss of two Rsa I fragments and the appearance of a new fragment of 421 residues was scored.

2.4. PROMOTER STRUCTURE

Protein expression is correlated with the level of RNA transcription which is regulated by DNA signals. Within the DNA are start (promoters) and stop (terminators) sequences for the RNA polymerase enzyme. The amount of transcription is regulated by the efficiency with which the RNA polymerase enzyme can recognize and then initiate and terminate transcription at specified signals.

Recognition, initiation and termination as well as the elongation process itself are all subject to RNA polymerase interaction with other components that can affect the process. Those components can include other proteins, e.g., in bacteria, sigma factor, CAP protein, repressors, and rho factor are part of the transcription process. Alternatively, the RNA polymerase can interact with the RNA product as occurs in transcription termination. In addition, the transcriptional efficiency is modulated by the concentrations of the precursor ribonucleotides that are present in the cell and the variations in their concentration that result from changes in physiological processes and growth conditions.

Much attention has been given the detailed sequence characteristics of the promoter. Bacterial promoters have been shown to bear significant homologies with each other. The strength of a particular promoter is significantly affected by its base sequence. The nucleotide sequences of 46 promoters were compared by Rosenberg and Court, Ann. Rev. Genet. 13: 319 (1979), who noted structural homologies in agreement with initial studies of others. Pribnow [Proc. Nat'l. Acad. Sci. 72: 784 (1975); J. Mol. Biol. 99: 419 (1975)] and Schaller et al. [Proc. Nat'l. Acad. Sci. 72: 737 (1975)] first noted a general consensus sequence TATAATG at a region about 10 bp from the start point of transcription, which is known as the −10 homology. The T residue in the sixth position of the −10 consensus sequence (emphasized supra) was invariant in those 46 promoters. More recent analysis of a special class of promoters, which regulate heat shock genes and are recognized by a special heat shock sigma factor rpoH, indicate that the −10 consensus varies dramatically from other promoters [Cowing et al., Proc. Nat'l. Acad. Sci. 82: 2679 (1985)]. That sequence consensus for six genes was CCCCATtTa and again a T was invariant (emphasized). The invariant T here however was surrounded by two poorly conserved bases (indicated in the consensus by lower case letters). Cowling et al. postulated that sigma factors may influence the interaction of RNA polymerase with DNA at the −10 region and/or interact with the DNA at that site themselves since consensus sequences for promoters recognized by different sigma factors from $T_4$, B. subtilis and E. coli varied considerably at the −10 region.

The other region demonstrating a consensus sequence amongst the 46 compared sequences was about 35 bp preceding the mRNA start point and was termed the −35 or recognition region as noted by Takanami et al. [Nature 260: 297 (1976)] and Seeburg et al., [Eur. J. Biochem. 74: 107 (1977)]. The consensus of the −35 region was t(g/c)TTGACA although within this sequence ACA was less conserved than TTG. The Cowing et al. heat shock −35 consensus TNtCNCcCTTGAA varied from the −35 consensus in that the heat shock sequence of other promotors was longer and had a C missing between the last two A nucleotides. The TTGA was however invariant.

Although it is not conserved in sequence, a structural motif, wherein the number of nucleotides between the −35 and −10 region is conserved, is present in bacterial promoters. Differences in spacing are apparent dependent on the type of sigma factor utilized and on the bacterial organism.

Studnicka [Biochem. J. 252: 825 (1988)] compared more than a 100 prokaryotic promoters compiled by others [Hawley and McClure, Proc. Nat'l. Acad. Sci. 77: 6381 (1980); Fournier and Ozeki, Microbiol. Rev. 49: 379 (1985);

Gentz and Bujard, J. Bacteriol. 164: 70 (1985); Mulligan et al., J. Biol. Chem. 260: 3529 (1985); Cowing et al., Proc. Nat'l. Acad. Sci. Proc. Nat'l. Acad. Sci. 82: 2679 (1985); Lindahl and Zengel, Ann. Rev. Genet. 20: 297 (1986)] using a computer analysis that computed a −10 region consensus and a −35 consensus. Studnicka's consensus was th . . . awwha.ttcTTGAcwt . . . t for the −35 region and . . . wt.tg.TAtAaTd . . .

for the −10 region where r=A/G, y=C/T, w=A/T, d=A/G/T, and h=A/C/T. Deviations from the consensus homologies for the −10 and −35 regions were plotted graphically on the X and Y axis respectively to correllate homology coefficients with the kinetics of binding and isomerization compiled by others using the abortive initiation assay developed by William McClure. From his calculations, Studnicka suggested that the primary effect of the spacing structural motif between the −35 and −10 region was upon the binding constant Kb. He also indicated that two different kinds of kinetic control might be achieved by varying the degree of homology to the consensus in the −10 and −35 region.

3. SUMMARY OF THE INVENTION

The present invention relates to expression of recombinant proteins by use of a bacterial host expression vector which expresses a recombinant protein under the control of a first regulatory expression element, and expresses a selectable marker under the control of a second regulatory expression element, which second element is mutated such that expression of the marker is at reduced levels relative to that directed by such an unmutated expression element. The invention provides expression vectors, host-vector expression systems (comprising the expression vector in a bacterial host in which it can be expressed), and methods relating thereto. Such an expression vector in a suitable bacterial host (a) allows ease of purification of the recombinant protein of interest ("the recombinant protein") since less selectable marker is present to interfere with the purification of the recombinant protein, and (b) increases the amount of recombinant protein that is produced by the bacterial host cell, thus improving yield. Furthermore, in an embodiment where the selectable marker encodes antibiotic resistance, the levels of antibiotic in the selection environment can only be used at the minimal possible levels that are necessary for selection. Higher levels of antibiotic result in cell destruction. Thus, such an expression vector ensures the use of the minimal levels of antibiotic, which is desirable in view of both environmental considerations and potential therapeutic use of the desired product.

3.1. DEFINITIONS

As used herein, the following terms shall have the indicated meanings:

| | |
|---|---|
| Ap | ampicillin |
| bp | base pair(s) |
| cDNA | complementary DNA |
| DNase | deoxyribonucleic acid nuclease |
| h | human |
| kD or kDa | kilo Dalton |
| kb | kilobases |

| | |
|---|---|
| Km | kanamycin |
| kanR | gene for Km resistance |
| KanR | protein for Km resistance |
| nt | nucleotide(s) |
| PBL | peripheral blood leukocytes |
| $P_L$ | Promoter left of lambda phage |
| $P_R$ | Promoter right of lambda phage |
| $P_{TAC}$, $P_{TRC}$ | Synthetic promoter of Tryptophan-lac combination |
| RBS or rbs | ribosome binding site |
| RNase | Ribonucleic acid nuclease |
| SDS | Sodium dodecylsulfate |
| TNF | tumor necrosis factor |
| (- - - -) | designates cells carrying plasmid - - - - |
| X-gal | Bromo-chloro-indolyl-β-D-galactopyranoside |

4. DESCRIPTION OF THE FIGURES

FIG. 1 shows a schematic of the general design of the vectors described in Section 7 infra. The plasmids used in these studies share the same basic elements: a promoter (p; narrow open box), a ribosome binding site (rbs; thick line), a recombinant gene to be expressed (open box), the replication region of pBR322 carrying a single nucleotide mutation (copI; blackened circle) that increases the copy number five-fold, and the kanamycin resistance gene (kanR; closed box). The four dots indicate the position of the kanR promoter that was modified by site-directed mutagenesis using the indicated, unique restriction sites.

FIG. 3 is a gel showing KanR and hTNF protein synthesis. Cells were precipitated from 0.5 ml aliquots of overnight cultures, lysed and loaded on 0.1% SDS-16% polyacrylamide gels. Lane C, W31101acI$^q$F$^-$; lane 1, W31101acI$^q$F$^-$ (ptk0); lane 2, W31101acIqF$^-$ (ptkl). The Mr's of protein markers (lane M, low-range standards, Biorad) are indicated, as well as the positions of the KanR and TNF proteins.

FIG. 4 shows KanR and PBL protein synthesis. Exponentially growing cultures were induced with 1% lactose and precipitated, lysed and loaded on 0.1% SDS-16% polyacrylamide gels. Aliquots were removed at 0, 7, and 17 hr after induction, as indicated. Lane M, marker proteins of low-range standards from Biorad. Lanes 1, 3 and 5: W3110lacI$^q$F$^-$ (pblkO); lanes 2, 4 and 6: W3110lacI$^q$F$^-$ (pblk1).

FIG. 5 shows plasmid levels before and after induction. Cultures were induced with 1% lactose and collected by centrifugation, resuspended, lysed and loaded on 1% agarose gels. Aliquots of cells were removed at 0, 7 and 17 hr after induction. Multimeric supercoiled forms can be seen for some of the plasmids. Chromosomal DNA appears at the top of the gel. The position of a 3900 bp restriction fragment marker is indicated. Lanes 1, 5 and 9: ptk0. Lanes 2, 6 and 10: ptk1. Lanes 3, 7 and 11: pblk0. Lanes 4, 8 and 12: pblk1.

5. DETAILED DESCRIPTION OF THE INVENTION

The present invention relates to expression of recombinant proteins by use of a bacterial host expression vector which expresses a recombinant protein under the control of a first regulatory expression element, and expresses a selectable marker under the control of a second regulatory expression element, which second element is mutated such that expression of the marker is at reduced levels relative to that directed by such an unmutated expression element. The invention provides expression vectors, host-vector expression systems (comprising the expression vector in a bacterial host in which it can be expressed), and methods relating thereto.

Such an expression vector in a suitable bacterial host allows ease of purification of the recombinant protein of interest ("the recombinant protein") since less selectable marker is present to interfere with the purification of the recombinant protein. In addition, one surprising advantage which the present invention provides is the increased production of the recombinant protein by the bacterial host cell, thus improving yield. Furthermore, in an embodiment where the selectable marker encodes antibiotic resistance, the present invention calls for and ensures the use of greatly reduced levels of antibiotic in the selection environment, desirable in view of both environmental considerations and potential therapeutic use of the desired product. The methods of the present invention also ensure selection of host cells containing maximum copy number plasmids, i.e., maximal producers. After mutation of the regulatory expression element for the selectable marker according to the present invention, any decrease in vector copy number results in reduced expression of plasmid gene products. The cells that have reduced vector copy number then die as they become sensitive to the remaining selective agent in the medium. The vector is thus maintained at high copy numbers on low concentrations of the selective agent.

Production of recombinant protein at high levels is a goal of genetic engineering. In addition to restrictions imposed during analytical characterization of vectors, the downstream processes of fermentation and protein purification impose restrictions on the development of commercial vectors that can be used for production of commercial quantities of bacterially expressed products. For example, present and anticipated regulations on recombinant products for therapeutic use preclude the use of certain antibiotics, e.g. ampicillin or derivatives thereof, as vector selection agents because of the possibility of contamination of the desired product with the antibiotic and its inadvertant administration to sensitive individuals. In addition, high level expression is best when the vector is present in high copy number to ensure that maximal levels of a desired product can be produced. However, maintaining high copy number vectors in a cell can be difficult, especially if the expressed product provokes any toxicity in cell metabolism. Current methods of plasmid maintenance include the use of very high concentrations of antibiotics to maintain a selective environment. The use of such high levels of antibiotic conflicts not only with the goals of regulatory agencies but also with the ease of purifying the expressed product.

Thus by reducing and minimizing the selectable marker production of commonly used expression vectors, the invention results in significant advantages over the present art: 1)

a major contaminant(s) of the desired product is greatly reduced, thus facilitating its purification; and 2) the net amount of the desired product in the producing organism can be increased, thus improving yield.

According to the present invention, reduced expression of the selectable marker encoded by the vector is accomplished by alteration (mutation) of a regulatory expression element which affects expression of the selectable marker. Various regulatory expression elements can be mutated according to the present invention. These control elements are any of a number of suitable transcription and translation elements that are active in bacteria.

Regulatory expression elements that can be altered include, but are not limited to, different elements of the promoter preceding the DNA sequence encoding the selectable marker such as the −10 and −35 region, or the spacing between the mRNA start site and the −10 region, or the spacing between the −10 and the −35 region; the ribosome binding site and/or the Shine/Dalgarno region (1975, Nature 254:34) of complementarity between the 16S rRNA and the mRNA; modification of the coding sequence of the selectable marker gene to reflect substitution of the naturally present codons for those coding for the same amino acid but that are present at low frequency in host proteins (decreased codon usage); modification of the codon for the ATG translation start site; increasing the secondary structure of the mRNA to mask the ribosome binding site and/or the Shine/Dalgarno region; increasing the instability of the mRNA by modification of the DNA sequence encoding the 3' end of the mRNA.

In a specific embodiment, the promoter directing the expression of the selectable marker is mutated by site directed mutagenesis to introduce mutations at selected nucleotides so as to disrupt the homology between the promoter and a proposed consensus sequence (see, e.g., Rosenberg and Court, 1980, Ann. Rev. Genet. 13: 319–353). In a preferred aspect of this embodiment, the foregoing manipulation also generates a convenient restriction enzyme recognition site for further genetic manipulations (e.g., for insertion of a different selectable marker).

Much attention has been given the detailed sequence characteristics of the promoter. The strength of a particular promoter is significantly affected by its base sequence. Bacterial promoters have bees shown to bear significant homologies with each other; such homologies can be disrupted according to the present invention to decrease expression directed by the promoter. Examples of such homologies, or consensus sequences, are discussed below.

The nucleotide sequences of 46 promoters were compared by Rosenberg and Court, Ann. Rev. Genet. 13: 319 (1979), who noted structural homologies and presented consensus sequences. Pribnow [Proc. Nat'l. Acad. Sci. 72: 784 (1975); J. Mol. Biol. 99: 419 (1975)] and Schaller et al. [Proc. Nat'l. Acad. Sci. 72: 737 (1975)] disclosed the general consensus sequence TATAATG at a region about 10 bp from the start point of transcription, which is known as the −10 homology. The T residue in the sixth position of the −10 consensus sequence (emphasized supra) was invariant in those 46 promotors. More recent analysis of a special class of promoters, which regulate heat shock genes and are recognized by a special heat shock sigma factor rpoH, indicate that the −10 consensus varies dramatically from other promoters [Cowing et al., Proc. Nat'l. Acad. Sci. 82: 2679 (1985)]. That sequence consensus for six genes was CCCCATtTa and again a T was invariant (emphasized). The invariant T here however was surrounded by two poorly conserved bases (indicated in the consensus by lower case letters). Sigma factors may influence the interaction of RNA polymerase with DNA at the −10 region and/or interact with the DNA at that site themselves since consensus sequences for promoters recognized by different sigma factors from T$_4$, B. subtilis and E. coli varied considerably at the −10 region (Cowling et al.; supra).

The other region demonstrating a consensus sequence amongst compared sequences is about 35 bp preceding the mRNA start point and is termed the −35 or recognition region (Takanami et al., Nature 260: 297 (1976); Seeburg et al., Eur. J. Biochem. 74: 107 (1977)). The consensus of the −35 region was t(g/c)TTGACA although within this sequence ACA was less conserved than TTG. The Cowing et al. heat shock −35 consensus TNtCNCcCTTGAA varied from the −35 consensus in that the heat shock sequence of other promotors was longer and had a C missing between the last two A nucleotides. The TTGA was however invariant.

Although it is not conserved in sequence, a structural motif, wherein the number of nucleotides between the −35 and −10 region is conserved, is present in bacterial promoters. Differences in spacing are apparent dependent on the type of sigma factor utilized and on the bacterial organism.

Studnicka [Biochem. J. 252: 825 (1988)] compared more than a 100 prokaryotic promoters compiled by others [Hawley and McClure, Proc. Nat'l. Acad. Sci. 77: 6381 (1980); Fournier and Ozeki, Microbiol. Rev. 49: 379 (1985); Gentz and Bujard, J. Bacteriol. 164: 70 (1985); Mulligan et al., J. Biol. Chem. 260: 3529 (1985); Cowing et al., Proc. Nat'l. Acad. Sci. Proc. Nat'l. Acad. Sci. 82: 2679 (1985); Lindahl and Zengel, Ann. Rev. Genet. 20: 297 (1986)] using a computer analysis that computed a −10 region consensus and a −35 consensus. Studnicka's consensus was th . . . awwha.ttcTTGAcwt . . . t for the −35 region and . . . wt.tg. TAtAaTd . . .

for the −10 region where r=A/G, y=C/T, w=A/T, d=A/G/T, and h=A/C/T. According to the present invention, deviations from such consensus homologies can be introduced to decrease expression under the control of the promoter.

For mutagenesis of a regulatory expression element, any technique for mutagenesis known in the art can be used, including both in vitro and in vivo mutagenesis techniques, including but not limited to in vitro site-directed or site-specific mutagenesis (see, e.g., Hutchinson, C., et al., 1978, J. Biol. Chem. 253: 6551; Matteucci and Heyneker, 1983, Nucl. Acids Res. 11: 3113, Derbyshire et al., 1986, Gene 46: 145; Oostra et al., 1983, Nature 304:456), use of TAB® linkers (Pharmacia), chemical mutagenesis, etc. In a preferred embodiment, in vitro site-directed mutagenesis is used.

The mutagenesis should be carried out so as to alter a regulatory expression element which regulates expression of the selectable marker but not expression of the recombinant protein, so to achieve reduced expression of the selectable marker using the mutated regulatory element, relative to the expression obtained using such an unmutated regulatory element. As used herein "mutated" shall mean "changed by deletion, insertion, substitution or modification of all or part of the nucleic acid sequence thereof." In a preferred embodiment, the mutation of the regulatory expression element results in expression of the selectable marker at the minimum level required for selection. Such a level can be easily determined using standard techniques known in the art.

As an example, selection of bacterial cells transformed with an expression vector containing the appropriately mutated regulatory expression element can be carried out as follows: First, the $EOP_{50}$ for the host bacterial cells (not transformed with the expression vector) is determined (using, e.g., the method of Tait et al., 1977, Mol. Gen. Genet. 151:327–331, or a modification thereof). The $EOP_{50}$ is the concentration of selective agent in the medium required to kill 50% of the host cells. The minimum amount needed for selection ("Quantity 1") (preferably the amount where 99% of the cells without the selectable marker (i.e. nontransformed) are killed) can then be estimated by one skilled in the art, based on the $EOP_{50}$ determination. (For example, one can estimate such amount to be 2–10× the $EOP_{50}$ concentration, where the selectable marker is an antibiotic resistance gene; a titration curve may be employed to more accurately determine the appropriate value for Quantity 1.) Second, the $EOP_{50}$ value is determined using host bacterial cells that have been transformed with an expression vector capable of expressing the selectable marker, in which a regulatory expression element for the selectable marker has not yet been mutated according to the present invention ("wild-type" vector) (this $EOP_{50}$ value, for cells transformed with wild-type vector, shall be termed "Quantity 2") The appropriate regulatory expression element of the vector is then mutated according to the present invention, such that when the bacterial host cells are transformed with the mutated vector, the concentration of selective agent in the medium required to kill approximately 99% of the background nontransformed cells is in between Quantity 1 and Quantity 2. Such concentration can be estimated from an experimental determination of the $EOP_{50}$ value for such cells. The closer such concentration (e.g., as reflected in the $EOP_{50}$ for cells transformed with the mutated vector) is to Quantity 1 (i.e. the lower such concentration), the more preferred is such mutated vector (since lower amounts of selective agent are needed in the medium for selection after transformation).

By way of illustration of the above, but not by way of limitation, where the selective agent is kanamycin, the $EOP_{50}$ can be determined (see Rothstein and Regnikoff, Cell 23:191 (1981)). For the bacterial strains described infra in Section 6 (*E. coli* W3110 lacI$^q$F$^-$ and MC1061), the $EOP_{50}$ was determined to be a few (~5) µg kanamycin per ml. Thus, the kanamycin concentration necessary to kill ~99% (nontransformed) host cells can be estimated to be ~10–50 µg/ml. For MC1061 cells carrying plasmid ptk1 (a "mutated" vector) or ptk0 (a "wild-type" vector) (the foregoing plasmids are described infra, in Section 6), the $EOP_{50}$ were found to be 40 µg/ml and >300 µg/ml kanamycin, respectively. These values are typical of most *E. coli* strains and consistant with the levels of kanamycin (10–50 µg/ml) typically used for plasmid selection (Sambrook, et al., Molecular Cloning, Cold Spring Harbor Laboratory Press (1989) pp. A6.) The $EOP_{50}$ for host cells transformed with ptk1 thus indicated that the vector was suitable for use according to the present invention.

In one embodiment of the invention, the promoter of the gene that is responsible for the transcription of a product that allows positive selection of the vector in cells is altered by site-specific mutagenesis. The altered promoter is less efficient in the process of transcription resulting in a decrease in the production of the product that allows selection. As a result, bacteria carrying the plasmid cannot be maintained on selective media at higher than the minimal necessary concentrations of selective agent.

In a further embodiment, the promoter of the gene for an antibiotic resistance marker is altered to result in decreased transcription of the gene for the antibiotic resistance marker. In a particular embodiment, the promoter regulating the kanamycin resistance gene is altered, resulting in selective growth of cells containing the vector on low concentrations of kanamycin ($\leq$20 µg/ml). The cells are unable to grow at higher concentrations of kanamycin (>30 µg/ml), in contrast to cells containing vectors that do not have the altered promoter regulating the kanamycin gene which are able to grow at concentrations of kanamycin in excess of 300 µg/ml.

Appropriately mutated regulatory expression elements, such that expression of the selectable marker is decreased, can be identified by methods known in the art. For example, where the mutation has been accomplished by site-directed mutagenesis, the desired clones can be identified by specific hybridization to the appropriate labeled probe (complementary to the mutated sequence). The clone can then be purified, e.g., by single-colony selection (see e.g., Grunstein and Hogness, 1975, Proc. Natl. Acad. Sci. U.S.A. 72:3961) after retransformation of the bacterial host, and the identity of the clone can be confirmed, e.g., by restriction enzyme analysis. Alternatively, the presence of the mutated regulatory element may be detected by observing the decreased expression of the selectable marker.

The selectable markers encompassed by the invention are selectable markers suitable for use in bacterial cells. Such selectable markers include the product of any gene that when present on a plasmid allows selective growth of the host in appropriate media. Examples of such selectable markers include but are not limited to antibiotic resistance gene products with selection in medium containing the antibiotic, including but not limited to the resistance genes for kanamycin, ampicillin, tetracycline, chloramphenicol, neomycin, gentamicin, penicillins (e.g., cephalosporin), mercury, erythromycin, lincomycin, a sulfonamide, trimethoprim, and derivatives of the foregoing (see Davies and Smith, 1978, Ann. Rev. Microbiol. 32:469, for commonly known antibiotic resistance genes); enzymes with selection in medium containing the enzyme substrate, where the enzyme reaction can be detected (including but not limited to the use of β-galactosidase with selection in medium containing lactose or galactose with host cells deleted for the lac operon, chloramphenicol acetyltransferase with selection in medium containing chloramphenicol; antigens with selection in medium containing antibody thereto; and suppressor transfer RNAs necessary for correct synthesis of essential bacterial gene products.

Any recombinant protein for which a nucleotide coding sequence can be obtained and expressed in bacteria can be expressed in the vector-host systems of the present invention. Similarly, any suitable selectable marker as discussed supra may be expressed by the vector-host systems of the present invention. The insertion of the desired recombinant protein sequence and desired selectable marker at the appropriate sites in the expression vector can be accomplished by knowledge common in the art. For example, the DNA fragment encoding the recombinant protein or selectable marker, as appropriate, may be ligated into a restriction enzyme recognition site on a vector which, upon digestion by the restriction enzyme, has the appropriate complementary cohesive termini. However, if the complementary restriction sites used to fragment the DNA are not present in the vector, the ends of the DNA molecule or of the vector site may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences.

Any of numerous bacterial host-expression vector systems known in the art can be employed in the practice of the present invention. The employed expression vector must be capable of replication and expression of both the recombinant protein and the selectable marker in the bacterial host. Thus, the vector must contain at a minimum a replicon. In addition, appropriate control elements (e.g. promoters, ribosome binding sites), regulating the expression of the recombinant protein and regulating the expression of the selectable marker must be present or introduced by sequence manipulations. The regulatory expression element for the selectable marker which is mutated according to the present invention to achieve reduced expression thereof, must not also regulate the expression of the recombinant protein, so that concomitant reduction in expression of the recombinant protein does not occur.

The vectors encompassed by this invention which can be modified according to the present invention to express a selectable marker at reduced levels while expressing a recombinant protein at substantially nonreduced or greater levels, are bacterial expression vectors, including but not limited to, naturally occurring plasmids such as plasmids like ColE1 (see e.g., Oka et al., 1979, Mol. Gen. Genet. 172: 151–159), F, R, etc.; bacteriophage such as lambdoid phages, λ, f1, Mu, phage 82, N4, P1, R17, M13, T7, T4, T3, Φ6, T1, P2, P4, P22, etc.; recombinant vectors made in the art such as pBR322, pSC100, pACYC, etc.; cosmids, or any of the other prokaryotic vectors known in the art such as pUC plasmid derivatives, (e.g., pUC8, pUC9, pUC18, pUC19), pBR325, pSP19, pT712, pT713, pSP64, pSP65, pGEM-1, pGEM-2, pGEM-3, pGEM-4, and modifications and derivatives of the foregoing, etc. Many such vectors are commercially available (e.g., Bethesda Research Laboratories, Gaithersburg, Maryland; New England Biolabs, Beverly, Massachusetts, Promega Biotec). (For examples of representative relevant publications relating to bacterial expression vectors, see Melton et al., 1984, Nucl. Acids Res. 12: 7035–7056; Peden, 1983, Gene 22:277; Young and Davis, 1983, Proc. Natl. Acad. Sci. U.S.A. 80: 1194–1198).

A variety of suitable promoters known in the art can be used in the expression vector to direct the expression of the recombinant protein or (with the mutated form of the promoter) the selectable marker, as the case may be. The promoter used to express the recombinant protein should be different from the promoter used to express the selectable marker. Promoters which can be used include but are not limited to the KanR promoter, the lactose operon (lac UV5) promoter of $E.\ coli$, the hybrid trp-lac UV-5 promoter (tac) (DeBoer, H., et al., 1982, in Promoter Structure and Function, Rodriguez, R. L. and Chamberlain, M. J., eds., Praeger Publishing, New York), the leftward ($P_L$) and the rightward ($P_R$) promoters of bacteriophage lambda, the bacteriophage T7 promoter, the trp operon promoter, the PI promoter (see U.S. Pat. No. 4,716,112 by Panayotatos), the lpp promoter (the $E.\ coli$ lipoprotein gene promoter; Nakamura, K. and Inouye, I., 1979, Cell 18: 1109–1117), etc. Other promoters produced by recombinant DNA or synthetic techniques may also be used to provide for transcription of the inserted sequences. Promoters may be inducible or constitutive. For expressing the selectable marker, in a preferred embodiment, a mutated form of the native promoter for the selectable marker is used (e.g., a mutated kanamycin resistance gene promoter is used to express the kanamycin resistance gene).

For expression vectors of the invention which have a high copy number (e.g., ~400 copies/cell, with a cop1 mutation), a relatively strong promoter (e.g., $\lambda P_L$, $\lambda P_R$, T7 promoter, tac, trc) should not be used, unless the host cell overexpresses a repressor for the promoter (e.g., use of the lacUV5 promoter in $E.\ coli$ W3110 lacI$^q$ which overexpresses the lac repressor), since optimal replication of the plasmid and expression of the recombinant protein cannot occur with such a strong promoter. Instead a relatively low-expression promoter (e.g., PI) should be used.

In contrast, in plasmids with a relatively low copy number (e.g., ~60 copies/cell; PBR322, for example), relatively strong promoters can be used. In such a low copy number vector, in a preferred embodiment, such a strong promoter is used to direct the expression of the recombinant peptide or protein according to the present invention.

In a preferred aspect of the invention, the expression vector also contains a mutation which causes high copy number, for example, the cop1 point mutation (see U.S. Pat. No. 4,716,112 by Panayotatos). Such a high copy number allows maximal expression of the recombinant peptide or protein.

The expression vector of the invention, comprising the recombinant protein sequence and the selectable marker sequence, each under control of the appropriate regulatory expression elements, should then be transferred into a bacterial host cell where it can replicate and be expressed. This can be accomplished by any of numerous methods known in the art including but not limited to transformation (e.g., of isolated plasmid DNA into the attenuated bacterial host), phage transduction (Schmeiger, 1972, Mol. Gen. Genetics 119:75), conjugation between bacterial host species, electroporation, etc.

U.S. Pat. No. 4,237,224 by Cohen and Boyer describes production of recombinant plasmids by cleavage with restriction enzymes and joining by use of DNA ligase. These recombinant plasmids are then introduced by means of transformation and replicated in unicellular cultures such as procaryotic organisms grown in tissue culture.

Another method for introducing recombinant DNA molecules into unicellular organisms is described by Collins and Hohn in U.S. Pat. No. 4,304,863. This method utilizes a packaging/transduction system with bacteriophage vectors (cosmids).

The bacterial hosts which can be used according to the present invention include varieties known in the art, incuding but not limited to strains of $Escherichia\ coli$, Bacillus species, Salmonella, and Shigella. In a preferred embodiment, $E.\ coli$ is used. The bacterial host should be compatible with the vector (e.g., its promoters and other regulatory elments) being used for expression, as is known to one skilled in the art. For example, plasmid pV1k1 (described in Section 6, infra) may be used in $E.\ coli$, but not in Bacillus.

Isolation of the recombinant protein can be by any technique known in the art for the purification of proteins, including but not limited to chromatography (e.g., high-pressure liquid chromatography, immunoaffinity, ion-exchange, and sizing column chromatography), centrifugation, differential solubility, isoelectric focusing, and two-dimensional gel electrophoresis.

Production of a recombinant peptide or protein according to the present invention provides additional advantages where the peptide or protein is therapeutically effective, since e.g., if the selectable marker is an antibiotic, the invention ensures that only minimal levels will be used in the production process. Thus, the present invention further provides pharmaceutical compositions comprising a recombinant peptide or protein produced by the methods of the invention, and a pharmaceutically acceptable carrier. Such a carrier includes but is not limited to any sterile biocompatible pharmaceutical carrier, such as saline, buffered saline, dextrose, and water.

For therapeutic use, the compositions of the invention can be formulated for a variety of modes of administration, including systemic and topical or localized administration (regarding techniques and formulations, see generally, *Remington's Pharmacetical Sciences*, Meade Publishing Co., Easton, Pa.).

For systemic administration, injection is preferred and may be intramuscular, intravenous, intraperitoneal, and subcutaneous. For injection, the compositions of the invention are formulated in liquid solutions, preferably in physiologically compatible buffers, such as Hank's or Ringer's. In addition, the compositions may be formulated in solid form and redissolved or suspended immediately prior to use. Lyophilized forms are also included.

Other methods of systemic administration include but are not limited to transmucosal, transdermal, or oral means. For transmucosal or transdermal administration, penetrants appropriate to the barrier to be permeated are known in the art and can be used in the formulation. Transmucosal administration may be through nasal sprays, for example. For oral administration, the compositions are formulated into conventional oral administration forms such as capsules, tablets, and tonics. For topical administration, the compositions of the invention are formulated into ointments, salves, gels, or creams, as generally known in the art.

In specific embodiments of the invention, the therapeutically effective protein is a neurotrophic molecule including but not limited to nerve growth factor, brain-derived neurotrophic factor (see e.g., Leibrook et al., 1989, Nature 341:149–152), or ciliary neurotrophic factor (see e.g., St öckli et al., 1989, Nature 342:920–923). In a particular embodiment, an expression vector of the invention can be used to express human ciliary neurotrophic factor.

6. EXAMPLE: RECOMBINANT PROTEIN PRODUCTION WITH MINIMAL-ANTIBIOTIC-RESISTANCE VECTORS

Commonly used expression vectors direct the synthesis of antibiotic-resistance proteins at unnecessarily high levels that complicate purification of the desired recombinant product. To overcome this problem, the promoter of the kanamycin-resistance gene (kanR) was altered by site-specific mutagenesis. As a result, synthesis of KanR protein was greatly reduced to the minimum required for host selection. At the same time, recombinant protein production was increased up to two-fold. Since the mutations did not alter any coding sequences and had no effect on plasmid copy number, the results indicate that plasmid-coded protein production can be limited, at least in part, by other genes expressed from the same plasmid. Because of the dependence of protein synthesis on gene dosage, minimizing antibiotic resistance allows continuous selection for cells harboring the maximum vector-copy number, thus ensuring maximal product synthesis.

6.1. MATERIALS AND METHODS

6.1.1. GENERAL TECHNIQUES

Enzymes including restriction enzymes, polynucleotide kinase and T4 DNA ligase were purchased from commercial sources (New England Biolabs) and used according to manufacturer's suggestions. Conditions for these enzymatic reactions are also found in Panayotatos and Wells, J. Biol. Chem. 254: 5555 (1979) and Panayotatos and Wells, J. Mol. Biol. 135: 91 (1979).

DNA was prepared for subsequent reactions by ether extraction, followed by EtOH precipitation. DNA electrophoresis in either agarose or polyacrylamide gels as performed as described by Panayotatos and Wells, id.

Protein gel electrophoresis was performed as described by Panayotatos and Fontaine, J. Biol. Chem. 260: 3173 (1985).

Cells were grown in Luria broth or yeast tryptone extract as described by Miller, Experiments in Molecular Genetics, Cold Spring Harbor Laboratory Press, 1972. Additional methods and other molecular cloning techniques were as described in Maniatis et al., Molecular Cloning, Cold Spring Harbor Laboratory Press, 1982. Oligodeoxynucleotides were synthesized using commercially available equipment (Applied Biosystems) as recommended by the supplier.

6.1.2. BACTERIAL STRAINS

*Escherichia coli* MC1061 is known in the art (Casadaban and Cohen, 1980, J. Mol. Biol. 138:179) and has been used in previous studies (Panayotatos, 1984, Nucl. Acids Res. 12:2641). *E. coli* W3110lacI$^q$F$^-$ was obtained from K. Hardy, Glaxo Research Institute (formerly Biogen SA), Geneva, Switzerland, as an F$^-$ derivative of *E. coli* W3110 lacI$^q$ (available from B. Beckman, *E. coli* Genetic Stock Center, Yale University).

6.1.3. PLASMIDS

Figure 1:
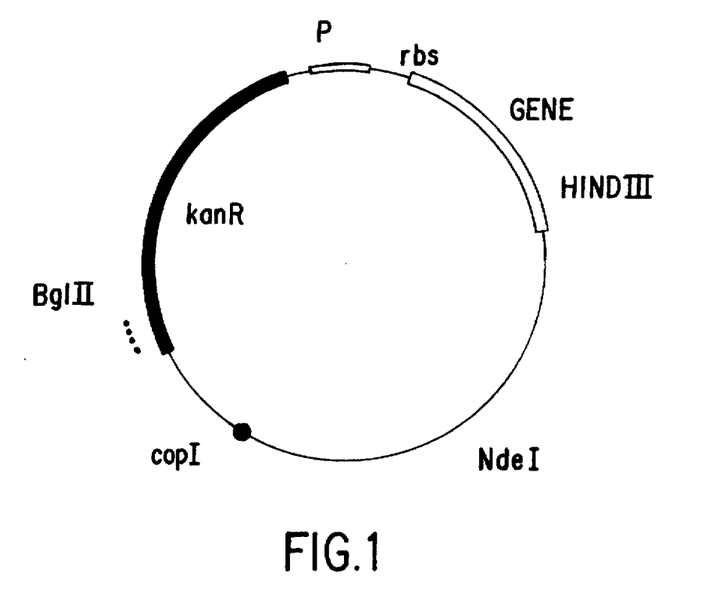

The plasmid vectors described in this application share the design shown in FIG. 1. These molecules were assembled using standard genetic engineering techniques.

Plasmid pPI.T7.tnf.cop1. Kan0 (abbreviated hereinafter as ptk0) comprises the following restriction fragments: 263 bp carrying the constitutive PI promoter (described in Panayotatos, Nucl. Acids Res. 12: 2641 (1984) and U.S. Pat. No. 4,716,112 issued Dec. 29, 1987); 112 bp coding for a phage T7 ribosomal binding site (as described in Panayotatos and Truong, Nucl. Acids Res. 9: 5679 (1981)); 689 bp consisting of the human tumor necrosis factor gene which is 471 bp and its downstream sequence as described in Fransen et al., Nucl. Acids Res. 13: 4417 (1985)); 2961 bp of the Sal I-Pst I restriction fragment from pBR322 carrying the cop1 point mutation (described in U.S. Pat. No. 4,716,112 by Panayotatos, and Panayotatos et al., J. Cell Biochem. Suppl. 7B:109 (1983); 1483 bp of the Hind III-Sal I restriction fragment from the left repeat of transposon Tn5 (see Auerswald et al., Cold Spring Harb. Symp. Quant. Biol. 45: 107 (1981); Beck et al., Gene 19: 327 (1982); and Rothstein and Reznikoff, Cell 23: 191 (1981)); and 72 bp of the Aat II-Eco RI restriction fragment from pBR322. The total length of the vector is 5580 bp.

Plasmid pPI.T7.tnf.cop1.kan0 (abbreviated ptk0) is identical to ptk0 except for a 4 nucleotide mutation introduced at the kanR promoter region by site-directed mutagenesis.

Plasmid pP5.T7.pbl.cop1.kanO (abbreviated: pblk0) comprises the following restriction fragments: 100 bp carrying the lacUV5 promoter (described in Panayotatos, Nucl. Acids Res. 12: 2641 (1984)); 112 bp coding for a phage T7 ribosome binding site; 555 bp consisting of 534 bp of a human gene of unknown function (termed "PBL") and its downstream sequence; 2763 bp of the Nru I-Pvu II restriction fragment from pBR322 carrying the cop1 mutation; 1483 bp of the Hind III-Sal I restriction fragment from the left repeat of transposon Tn5; and 72 bp of the Aat II-Eco RI restriction fragment of pBR322. Total plasmid length: 5085 bp.

Plasmid pP5.T7.pbl.cop1.kanl (abbreviated pb1k1) is identical to pb1k0 except for the same 4 nucleotide mutation in the kanR promoter region, as in ptk1.

Plasmid pV1k1 is a general vector that exploits the advantages of this invention for gene expression. It was constructed as follows: a 2,870 bp EcoRI-Nde I restriction fragment was isolated from plasmid ptkl using the established techniques of agarose gel electrophoresis, electroelution and ethanol precipitation. Using the same techniques, a 1,760 bp EcoRI-Nde I fragment was isolated from pNKS97 (Panayotatos and Truong, 1981, Nucl. Acids Res. 9: 5679–5688). The two fragments were then ligated together, and the resultant plasmid was used to transform *E. coli* W3110lacI$^q$. Plasmid DNA was prepared from colonies selected on kanamycin plates and characterized by restriction mapping. The characterized plasmid, designated pV1k1, constitutes a vector engineered to express minimal resistance to kanamycin and to accept foreign genes for expression by minimal further genetic manipulation, by insertion into its convenient SalI site or any genetic modification thereof. (For example, nucleotide sequences comprising a convenient restriction enzyme recognition site ("linker molecule") can be inserted at the SalI site and used for insertion of a heterologous gene with the appropriate complementary base termini, by techniques known in the art.) A suitable strain hosting this plasmid, *E. coli* W3110lacI$^q$/pV1k1 has been deposited with an international microorganism depository (see Section 8, infra).

Although the plasmids described in this section have either the human TNF gene or the human PBL gene inserted after the ribosomal binding site and ATG start codon, these DNA gene sequences are merely illustrative of the recombinant gene that may be inserted in the vector. The invention is not limited or restricted to the examples provided as particular embodiments of inserted recombinant proteins. The proteins given as examples are provided to illustrate the invention and its utility in high level expression of recombinant proteins. The examples are not to be construed as limiting the scope of the invention, which scope is determined by this entire specification including the appended claims.

6.2. RESULTS

Commonly used expression vectors direct the synthesis of antibiotic resistance proteins at unnecessarily high levels that complicate purification of a desired overproduced protein which may be a recombinant protein. Promoters of antibiotic resistance genes, which are used for vector selection after transformation of cells, can be altered by site-specific mutagenesis. The alteration in the antibiotic resistance gene promoter in the present example did not alter any sequences that were encoded by protein, and had no effect on plasmid copy number. As a result of the alteration, the synthesis of the protein encoded by the antibiotic resistance gene was greatly reduced to the minimum required by vector selection after host transformation.

One unexpected and surprising advantage of the promoter alteration was that the product of the recombinant gene that was also encoded by the vector plasmid, but which had no alterations in its nucleotide sequence or control regions, was increased in amount up to two fold as compared to vectors that had no alteration in the antibiotic resistance gene promoter. The change in the promoter of the antibiotic resistance gene had the other expected advantage of ensuring the continuous selection for cells harboring the maximum vector-copy number. Selection for cells with maximum vector-copy number ensures maximal product synthesis since the efficiency of protein expression is directly correlated with the number of copies of the gene of the desired protein, as well as with the rates of transcription, translation and degradation of the desired gene's mRNA and protein products.

6.2.1. SITE-DIRECTED MUTAGENESIS OF THE PROMOTER FOR THE KANAMYCIN RESISTANCE GENE (KanR)

Figure 2:
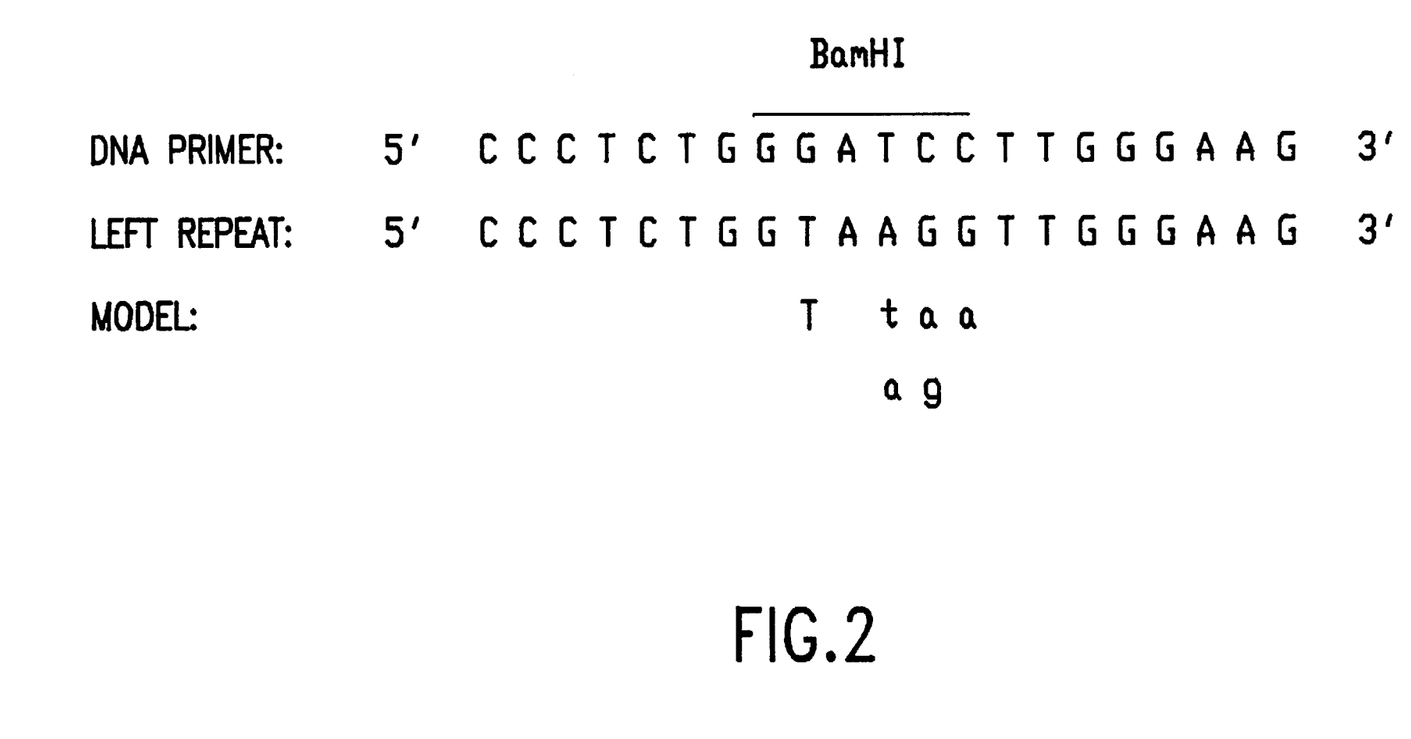
FIG. 2 shows the nucleotide sequence at the kanR promoter region. The left repeat sequence of the kanR gene was modified by site-directed mutagenesis using the oligodeoxynucleotide primer shown in the upper line. The mutation generates the indicated Bam HI restriction site. The model promoter sequence shows the most frequently encountered nucleotides (t,a,g) at the mutated positions.

Plasmid ptk0 contains the promoter, ribosome binding site and the kanR gene sequence of the left inverted repeat of transposon Tn5. Using site-directed mutagenesis, four mutations were introduced at selected nucleotides of the promoter as shown in FIG. 2, where the GGTAAGGTT sequence of the kan left repeat containing a portion of the promoter for RNA polymerase was changed to GGGATCCTT. The mutations were designed to disrupt the homology between the kanR promoter and a proposed consensus sequence and to generate a Bam HI restriction site for future manipulations. A 21 nucleotide synthetic oligodeoxynucleotide of the desired sequence as shown in FIG. 2 was added to a reannealed mixture of a 3935 bp Nde I-Bgl II fragment from ptk0 and a full-length 5580 bp Hind III fragment of the same plasmid. Subsequent steps were as described by Oostra et al., Nature 304:456 (1983).

Positive clones were identified by hybridization against radioactively labeled primer at 65° C. and purified by single colony selection after re-transformation. The identity of the final plasmid ptk1 was established by extensive restriction enzyme analysis that confirmed the generation of a unique Bam HI site at the expected position.

6.2.2. DECREASE IN KANAMYCIN RESISTANCE

*E. coli* MC1061 cells transformed with ptkl grew normally on agar containing 15 µg kanamycin per ml but could not survive at higher concentrations. In contrast, cells containing ptk0 grew easily at 300 µg kanamycin per ml. The concentration of kanamycin needed to kill 50% of the cells, i.e. the concentration needed to provide a 50% efficiency of plating ($EOP_{50}$), was determined according to Rothstein and Reznikoff Cell 23: 191 (1981). The $EOP_{50}$ was >300 µg/ml for MC1061 (ptk0) and 40 µg/ml for MC1061 (ptk1) cells. The resistance conferred to the host by the high-copy-number plasmid ptkl is just sufficient to allow selection at the minimum (10–20 µg/ml) working concentration of kanamycin. Since antibiotic resistance depends on gene dosage, lower-copy-number plasmids which express the kanamycin resistance gene at the same levels should not confer resistance to their host. Indeed, attempts to exchange the pBR322/cop1 replicon in ptk1 with the lower-copy pBR322 replicon were not successful, even though this exchange was performed routinely with ptk0 that carries the wild-type kanR promoter. Thus, by introducing four mutations in the promoter region of the kanR gene, lowered resistance to the minimum level required for selection of the ptkl plasmid, present at 200 copies per cell, was achieved. Direct visualization of the KanR protein confirmed that synthesis of the KanR protein was reduced as a result of the promoter mutations as demonstrated in FIG. 3.

Figure 3:
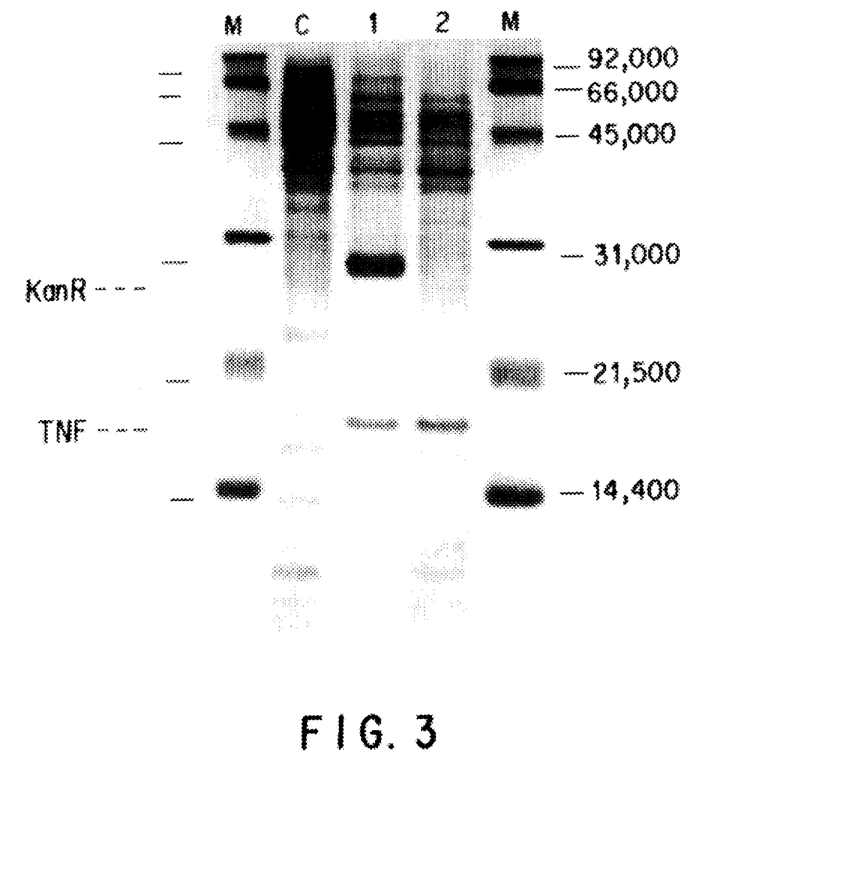

W31101lacI$^q$F$^-$ (ptk0) cells produce the KanR protein at 5–10% of total cellular protein as determined from the band intensities of protein gels in lane 1 of FIG. 3. In contrast, W31101lacI$^q$F$^-$ (ptk1) cells do not produce a detectable band at the corresponding position of the gel, as shown in lane 2 of FIG. 3, indicating that KanR is synthesized at levels below the detection limit of the gel (≦0.2%). Thus, the mutated kanR promoter in ptk1 is at least 50 times less active than the wild-type left repeat promoter in ptkO. This experiment shows the distinct practical advantage of decreasing the synthesis of KanR protein by alteration of the kanR gene's promoter, in that a major contaminant of protein purification, the KanR protein, is essentially eliminated.

To confirm that the KanR protein production was not the result of read-through transcription but was the result of transcription initiated at the mutated promoter, the nucleotide sequence between Bgl II and a Pvu II site 92 bp upstream was deleted. This manipulation should destroy the kanR promoter without affecting the ribosome binding site and gene sequences (Auerswald et al., 1981, Cold Spring Harbor Symp. Quant. Biol. 45: 107–113; Beck et al., 1982, Gene 19: 327–336; Berg et al., 1975 Proc. Natl. Acad. Sci. U.S.A. 72: 3628–3632; Rothstein and Reznikoff, 1981, Cell 23: 191–199), so that only read-through transcription could substitute for promoter function. No kanamycin resistant colonies could be detected in two independent attempts, suggesting that read-through transcription could not account for the low kanamycin resistant activity observed with ptkl.

Comparison of the results in FIG. 3 also shows that similar levels of hTNF are synthesized with either ptk0 or ptk1, although the percentage of total protein which is hTNF increases with the use of ptk1. Thus, the mutations in the kanR promoter caused a drastic decrease in antibiotic resistance but did not affect recombinant protein production. In this case, the main practical advantage that renders ptk1 a superior expression vector is the elimination of a major contaminant of protein purification.

6.2.3. RECOMBINANT PROTEIN PRODUCTION

Comparison of the expression of different recombinant proteins in the expression vectors was accomplished by replacing the hTNF DNA sequence in ptk1 with a gene for a protein of unrelated sequence and of unknown function termed PBL. The resultant plasmid pb1k1 shares the basic design, shown in FIG. 1 except that transcription of the human gene is regulated by the lacUV5 promoter. As a control, the same sequence was introduced into ptk0 to generate pb1k0. The restriction fragments making up each plasmid are specifically described supra.

Figure 4:
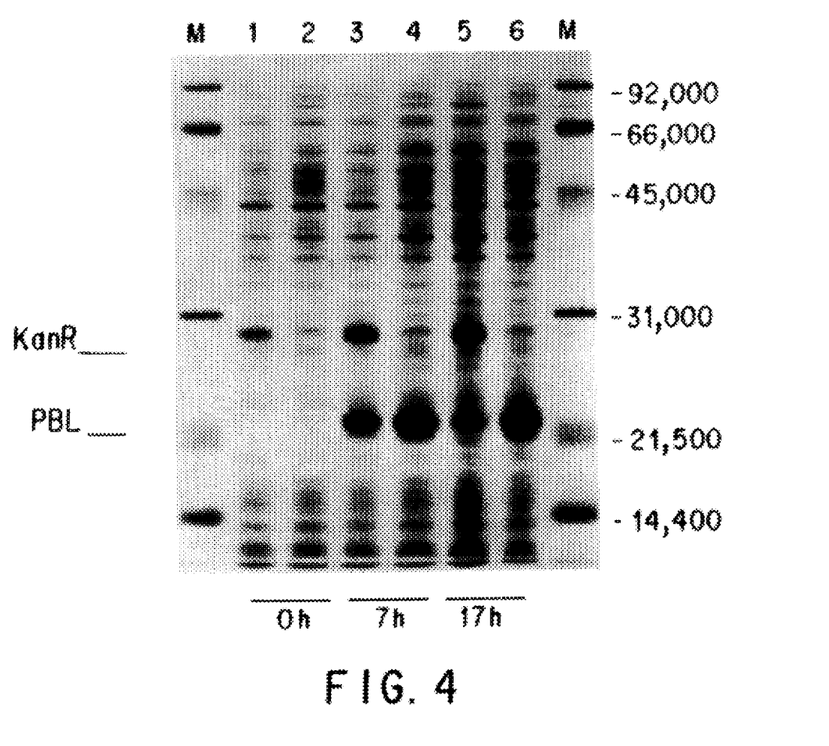

E. coli W3110lacI$^q$F$^-$ cells harboring each plasmid were grown to mid-exponential phase and induced with lactose. Extracts of total protein were prepared at various times and analyzed by gel electrophoresis. Comparison of the relevant band intensities in FIG. 4 shows that in W3110lacI$^q$F$^-$ (pb1k1) cells, high levels of recombinant protein are present 7 hr after induction and even higher levels are present at 17 hr (lanes 2, 4, and 6). Undetectable levels of KanR protein are present in these cells. In contrast, high levels of KanR protein are present in W3110lacI$^q$F$^-$ (pb1k0) cells (lanes 1, 3, and 5). In these cells production of recombinant protein appears to peak 7 hr after induction.

At each time point, more recombinant protein is present in cells hosting pb1k1 than in cells hosting pb1k0. In late stationary cells hosting pb1k0, the two highly expressed plasmid-coded proteins, i.e. the KanR protein and the recombinant protein, together constitute approximately 50% of total cellular protein. In contrast, in cells containing pb1k1, the recombinant protein alone is produced at that level (FIG. 4, lanes 5 and 6). Thus mutagenesis of the kanR promoter in pb1k1 generates minimal levels of KanR protein but, surprisingly, higher levels of recombinant protein. The results indicate that for this recombinant protein, production is limited by other proteins expressed from the same plasmid at high levels. Minimization of promoter activity minimizes competition and allows production of higher levels of the desired protein where plasmid copy number remains the same (since gene expression also depends on gene dosage).

Figure 5:
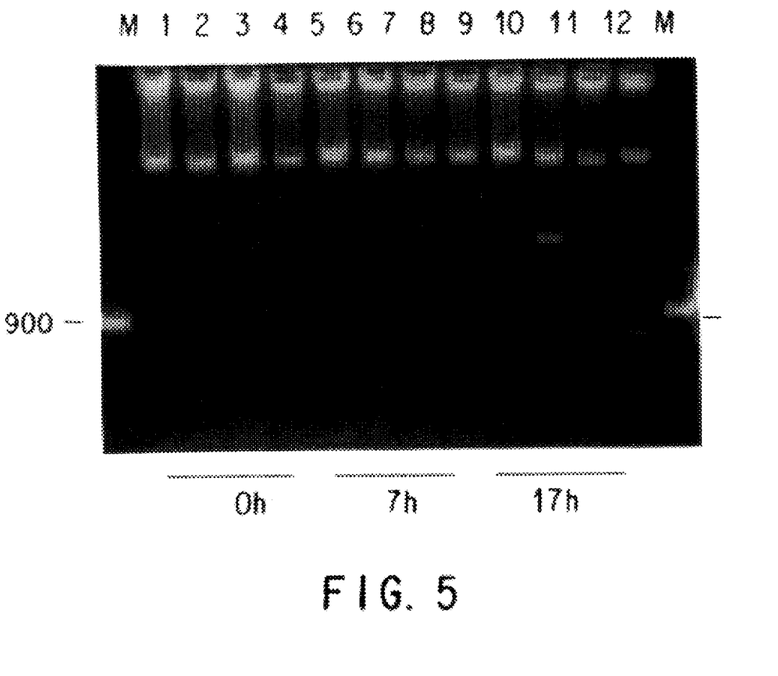
Figure 6:
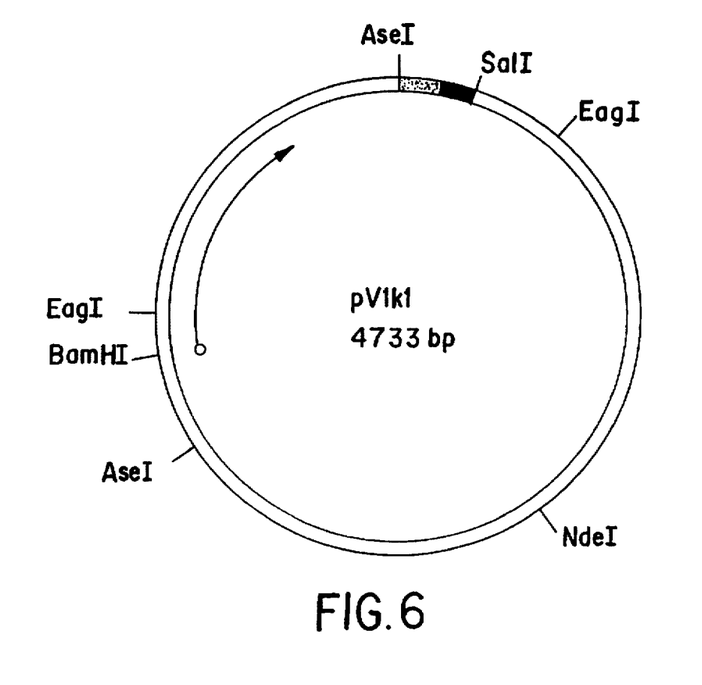
FIG. 6 shows a schematic of the general vector p.lac.T7.v.copI.kanl (abbreviated pV1k1). Solid bar: ribosome binding site; speckled bar: promoter region; arrow: kan1 resistance gene; open circle: kan1 promoter

The copy numbers of the four plasmids were expected to be the same at least under the conditions of the experiments described in FIGS. 3 and 4, in the absence of antibiotic pressure. The plasmid levels were determined experimentally as shown in FIG. 5, which shows that the mutations of the kanR promoter have no detectable effect on copy number, allowing the direct comparison of the KanR protein and the recombinant protein levels in the same hosts, as was done in the experiments shown in FIG. 3 and 4.

6.3. DISCUSSION

The pair of high kanR plasmids, ptk0 and pb1k0, differ from their minimal kanamycin resistance counterparts, ptk1 and pb1k1, only by the mutations at the kanR promoter region. Since these mutations fall outside the coding sequence and have no effect on plasmid copy number, minimal resistance is the direct result of reduced promoter activity rather than an indirect effect of decreased mRNA or protein stability.

The reduction of KanR protein synthesis had an unexpected effect on recombinant protein production. Higher levels of hPBL protein were observed when KanR protein was reduced, particularly in late stationary cultures. Minimal resistance vectors thus have the advantage of allowing increased recombinant protein production; this may be due to competition for the synthetic machinery of the cell between the levels of recombinant and antibiotic resistance proteins, or other highly expressed plasmid coded proteins, especially those that are produced as selective markers of the vector. Such competition can result from the competition of the two genes for RNA polymerase, for competition between the mRNAs of the genes for translation, from the stability of the mRNAs of the two proteins, or from the stability of the two proteins themselves.

In the case of TNF which is produced at relatively low levels, the fact that an increase to the same extent is not observed between ptk0 and ptk1 is not inconsistent with this interpretation. Production of hTNF with either plasmid is not limited by the strength of the RNA I promoter which is at least as strong as lacUV5 and has led to the production of high levels of other recombinant proteins (Panayotatos, 1984, Nucl. Acids. Res. 12:2641–2648; U.S. Pat. No. 4,716, 112 by Panayotatos). Factors limiting TNF production are probably related to the efficiency of translation and/or the stability of the mRNA and the protein.

7. EXAMPLE: SITE-SPECIFIC MUTAGENESIS OF THE AMPICILLIN RESISTANCE GENE PROMOTER

The most common expression vectors are either derived from pBR322 (Bolivar et al., 1977, Gene 2:95–113; Sutcliffe, 1979, Cold Spring Harbor Symp. Quant. Biol. 43:77–90) or have copy numbers in the same range of 20–60 per cell. Such plasmids confer to their host resistance up to 5 mg ampicillin (Ap) per ml, whereas five times higher copy number mutants can confer resistance to at least 20 mg Ap/ml (Wong et al., 1982, Proc. Natl. Acad. Sci. U.S.A. 79:3570–3574; Panayotatos, 1984, Nucl. Acids Res. 12:2641–2648; U.S. Pat. No. 4,716,112). These levels are far in excess of those required for plasmid selection (20–50

µg Ap/ml). At the same time, the protein responsible for antibiotic resistance (β-lactamase) is present at levels between 0.2% and 5% of total cellular protein depending on the particular gene and copy number of the plasmid.

To minimize the level of both mRNA and protein expression of the β-lactamase gene, one can alter the DNA sequence in the −10 region of the P3 promoter (Brosins et al., 1982, J. Biol. Chem. 257:9205) of plasmid pNKS97 cop⁻ (Panayotatos, N., 1987, in Plasmids: A Practical Approach, IRL Press, Oxford, U.K., pp. 163–176). Alternatively, one can start with the plasmid PBR322, delete the 650 bp EcoRI-SalI fragment, introduce a high copy number mutation, and alter the DNA sequence in the −10 region of the P3 promoter. Examples of such mutations to the −10 region of the P3 promoter, and their comparison with the wild-type promoter and consensus −10 region sequence of Studnicka (Biochem. J. 252:825 (1988)) are shown below:

| | |
|---|---|
| consensus | w t. t g . T A t A a T d . . |
| wild-type | T C . T G A G A C A A T A . . |
| "down" mutant 1 | T C . T C T A G A A A T A . . |
| "down" mutant 2 | T C . T C T A G A G A T A . . |
| "down" mutant 3 | T C . T C T A G A G G T A . . |
| New unique site | XbaI |

These mutations are introduced either by site-specific mutagenesis or by a Polymerase Chain Reaction (PCR) approach taking advantage of the nearby unique SspI and AatII or EcoRI restriction sites. Either approach requires the use of synthetic oligodeoxynucleotides. In all cases, mutated plasmids are transfered into $E.$ $coli$ and the $EOP_{50}$ levels for ampicillin determined as described (Rothstein and Regnikoff, 1981, Cell 23:191). The ampicillin concentration in the medium which kills ~99% of (nontransformed) $E.$ $coli$ W3110lacI$^q$ cells is ~40 µg Ap/ml (based on a $EOP_{50}$ value of ~15 µg Ap/ml). The $EOP_{50}$ value for such host cells transformed with a "wild-type" vector (containing the unmutated P3 promoter) is ~10,000–50,000 µg Ap/ml. Thus, mutated vectors are selected which, upon transformation into the host cells, result in an $EOP_{50}$ in between 50 and 5000 µg Ap/ml, and preferably −100–150 µg Ap/ml or less.

8. DEPOSIT OF MICROORGANISM

The following plasmid bearing cell strain was deposited with the Agricultural Research Culture Collection (NRRL), Peoria, Ill. and has been assigned the indicated accession number:

| Strain | Date of Deposit | Accession Number |
|---|---|---|
| E. coli W3110lac$^q$F⁻ bearing plasmid pV1k1 | January 23, 1990 | B-18600 |

The present invention is not to be limited in scope by the microorganism deposited since the deposited embodiment is intended as an illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair and amino acid residue numbers and sizes given for nucleotides and peptides are approximate and are used for purposes of description. Various references are cited herein, the disclosures of which are incorporated by reference herein, in their entireties.

What is claimed is:

1. A method of minimizing expression of a selectable marker from a bacterial expression vector comprising mutating a promoter in the expression vector, which promoter, in a Escherichia coli cell, regulates the expression of a first vector sequence encoding the selectable marker, said mutating being such that when expression of the first vector sequence encoding the selectable marker is regulated by the mutated promoter in the Escherichia coli cell, there is decreased expression of the selectable marker relative to the expression of the selectable marker when the promoter is not so mutated, wherein the decreased expression of the selectable marker (i) increases the percentage of a peptide or protein encoded by a second vector sequence in the total protein relative to the percentage of the peptide or protein in the total protein when the promoter is not so mutated, or (ii) increases the production of the peptide or protein encoded by the second vector sequence relative to the production of the peptide or protein when the promoter is not so mutated, and wherein the selectable marker promotes the survival of the Escherichia coli cell in the presence of a selective agent that is toxic to the Escherichia coli cell.

2. The method according to claim 1 in which the selectable marker is a peptide or protein conferring resistance to an antibiotic upon the Escherichia coli cell.

3. The method according to claim 2 in which the antibiotic is selected from the group consisting of kanamycin, ampicillin, tetracycline, and chloramphenicol.

4. The method according to claim 1 in which the promoter is selected from the group consisting of the lac UV5 promoter, kanamycin resistance gene promoter, tac promoter $\lambda P_L$, $\lambda P_R$, bacteriophage T7 promoter, trp promoter, PI promoter, and the lpp promoter.

5. A method for producing a recombinant peptide or protein comprising growing an Escherichia coli cell containing an expression vector, said vector having a nucleic acid sequence which comprises (a) a first promoter controlling, when the vector is in the cell, the expression of the recombinant peptide or protein; (b) a sequence encoding the recombinant peptide or protein; (c) a second promoter controlling, when the vector is in the cell, the expression of a selectable marker; and (d) a sequence encoding the selectable marker; in which the second promoter is mutated such that when the vector is in the cell the expression of the selectable marker is reduced relative to the expression of the selectable marker when the second promoter is not so mutated, and in which both the recombinant peptide or protein and the selectable marker are expressed in the cell, wherein the reduced expression of the selectable marker (i) increases the percentage of the recombinant peptide or protein in the total protein relative to the percentage of the recombinant peptide or protein in the total protein when the second promoter is not so mutated, or (ii) increases the production of the recombinant peptide or protein relative to the production of the recombinant peptide or protein when the second promoter is not so mutated, and wherein the selectable marker promotes the survival of the Escherichia coli cell in the presence of a selective agent that is toxic to the Escherichia coli cell.

6. The method according to claim 5 in which the selectable marker is a peptide or protein conferring resistance to an antibiotic upon the Eshcerichia coli cell.

7. The method according to claim 6 in which the antibiotic is selected from the group consisting of kanamycin, ampicillin, tetracycline, and chloramphenicol.

8. The method according to claim 6 in which the antibiotic is kanamycin.

9. The method according to claim 5 in which the second promoter is selected from the group consisting of the kanamycin resistance gene promoter, the neomycin resistance gene promoter, and the gentamicin resistance gene promoter.

10. The method according to claim 5 in which the second promoter is the kanamycin resistance gene promoter.

11. The method according to claim 5 in which the first promoter is selected from the group consisting of the lac UV5 promoter, tac promoter, $\lambda P_L$, $\lambda P_R$, bacteriophage T7 promoter, trp promoter, PI promoter, and the lpp promoter.

12. The method according to claim 10 in which the first promoter is the lac UV5 promoter.

13. The method according to claim 10 in which the first promoter is the PI promoter.

14. The method according to claim 5 in which the expression vector further comprises a mutation causing high vector copy number.

15. The method according to claim 6 in which the expression vector further comprises a mutation causing high vector copy number.

16. The method according to claim 7 in which the expression vector further comprises a mutation causing high vector copy number.

17. The method according to claim 8 in which the expression vector further comprises a mutation causing high vector copy number.

18. The method according to claim 14 in which the mutation causing high vector copy number is the cop1 mutation.

19. The method according to claim 15, 16 or 17 in which the mutation causing high vector copy number is the cop1 mutation.

* * * * *